(12) United States Patent
Murphy et al.

(10) Patent No.: US 12,208,155 B2
(45) Date of Patent: Jan. 28, 2025

(54) METHOD FOR IMPROVING DURATION OF EFFECT OF DERMAL FILLER TREATMENT

(71) Applicant: Allergan, Inc., Irvine, CA (US)

(72) Inventors: Diane K. Murphy, Goleta, CA (US); Deepali Paradkar-Mitragotri, Santa Barbara, CA (US)

(73) Assignee: Allergan, Inc., Irvine, CA (US)

( * ) Notice: Subject to any disclaimer, the term of this patent is extended or adjusted under 35 U.S.C. 154(b) by 745 days.

(21) Appl. No.: 16/702,449

(22) Filed: Dec. 3, 2019

(65) Prior Publication Data
US 2020/0101003 A1    Apr. 2, 2020

Related U.S. Application Data

(62) Division of application No. 14/929,053, filed on Oct. 30, 2015, now Pat. No. 10,493,014.
(Continued)

(51) Int. Cl.
*A61K 8/73* (2006.01)
*A61K 8/04* (2006.01)
(Continued)

(52) U.S. Cl.
CPC .............. *A61K 8/735* (2013.01); *A61K 8/042* (2013.01); *A61K 31/728* (2013.01); *A61L 27/20* (2013.01);
(Continued)

(58) Field of Classification Search
CPC ......... A61M 31/00; A61M 5/178; A61K 9/14; A61K 31/78; A61K 8/735; A61K 8/042;
(Continued)

(56) References Cited

U.S. PATENT DOCUMENTS

| 8,286,639 | B2 * | 10/2012 | Seckel | A61Q 19/08 |
| | | | | 601/17 |
| 8,475,815 | B2 * | 7/2013 | Boutros | A61K 9/1652 |
| | | | | 424/501 |

(Continued)

FOREIGN PATENT DOCUMENTS

| WO | WO-2012024635 A2 * | 2/2012 | ............. A61B 5/442 |

OTHER PUBLICATIONS

Alsarraf, "Outcomes Instruments in Facial Plastic Surgery," Facial Plastic Surgery, 2002, 77-86, vol. 18, No. 2, Thieme Medical Publishers, Inc.
(Continued)

*Primary Examiner* — Ann Schillinger
(74) *Attorney, Agent, or Firm* — Mintz, Levin, Cohn, Ferris, Glovsky and Popeo, P.C.

(57) ABSTRACT

A method of treating midface volume deficit in a person is provided. The method generally includes administering a dermal filler, such as a hyaluronic acid based dermal filler, in a sequence of injections that enhance effectiveness and/or duration of the filler. The method may include initially introducing a volume of the filler into at a zygomaticomalar region of the face prior to introducing one or more additional volumes of the filler into the anteromedial region and the submalar region, such that the duration of effectiveness of the treatment is improved, and less filler is required to achieve a desired correction.

14 Claims, 9 Drawing Sheets

Related U.S. Application Data (60) Provisional application No. 62/073,786, filed on Oct. 31, 2014, provisional application No. 62/115,705, filed on Feb. 13, 2015.

(51) Int. Cl.
    *A61K 31/728*     (2006.01)
    *A61L 27/20*     (2006.01)
    *A61L 27/50*     (2006.01)
    *A61L 27/52*     (2006.01)
    *A61Q 19/08*     (2006.01)

(52) U.S. Cl.
CPC .............. *A61L 27/50* (2013.01); *A61L 27/52* (2013.01); *A61Q 19/08* (2013.01); *A61K 2800/884* (2013.01); *A61K 2800/91* (2013.01); *A61L 2400/06* (2013.01); *A61L 2430/34* (2013.01)

(58) Field of Classification Search
CPC ............ A61K 31/728; A61K 2800/884; A61K 2800/91; A61K 9/0019; A61L 27/20; A61L 27/50; A61L 27/52; A61L 2400/06; A61L 2430/34; A61Q 19/08; A61P 17/00; A61P 43/00
See application file for complete search history.

(56) References Cited

U.S. PATENT DOCUMENTS

| | | | | |
|---|---|---|---|---|
| 8,672,918 | B2* | 3/2014 | Barbour ................. | A61K 38/39 600/587 |
| 8,778,909 | B2* | 7/2014 | Wortzman ............. | A61K 8/735 424/422 |
| 8,815,228 | B2* | 8/2014 | Boutros ................. | A61K 8/735 424/78.31 |
| 8,956,632 | B2* | 2/2015 | Boutros ................. | A61L 27/16 424/401 |
| 10,493,014 | B2* | 12/2019 | Murphy ................. | A61K 8/735 |
| 2004/0225276 | A1* | 11/2004 | Burgess ................. | A61L 27/18 604/506 |
| 2009/0204101 | A1* | 8/2009 | Wortzman ............. | A61Q 19/08 604/93.01 |
| 2010/0136070 | A1* | 6/2010 | Dobak ................... | A61K 8/733 424/602 |
| 2014/0039062 | A1* | 2/2014 | Stroumpoulis ..... | C08B 37/0072 514/777 |

OTHER PUBLICATIONS

American Society for Aesthetic Plastic Surgery, Cosmetic Surgery National Data Bank Statistics, The American Society for Aesthetic Plastic Surgery, 2012, Accessed Oct. 1, 2014, http://www.surgery.org/sites/default/files/ASAPS-2012-Stats.pdf.

ASDS Survey: Consumers Rate Soft-Tissue Treatments Tops; Choose Dermatologic Surgeons Most Often for Procedure, American Society for Dermatologic Surgery, 2013, 2 pages.

Brody, "Use of Hyaluronidase in the Treatment of Granulomatous Hyaluronic Acid Reactions or Unwanted Hyaluronic Acid Misplacement," Dermatologic Surgery, 2005, 893-7, 31(8 Pt 1), BC Decker Inc.

Callan et al., "Efficacy and safety of a hyaluronic acid filler in subjects treated for correction of midface volume deficiency: a 24 month study," Clinical, Cosmetic and Investigational Dermatology, Mar. 20, 2013, 81-89, 6, Dovepress.

Few, "Voluma: Vital Considerations for Use in Midface Lifting," Plastic Surgery Pulse News, vol. 5, No. 3, 2013, pp. 1-3.

Fischer, "A European evaluation of cosmetic treatment of facial volume loss with Juvederm Voluma in patients previously treated with Restylane Sub-Q," Journal of Cosmetic Dermatology, 2010, 291-296, 9, Wiley Periodicals, Inc.

Gierloff et al., "Aging Changes of the Midfacial Fat Compartments: A Computed Tomographic Study," Plastic and Reconstructive Surgery, Jan. 2012, 263-273, 129, American Society of Plastic Surgeons.

Hanke et al., "Facial Soft-Tissue Fillers Conference: Assessing the State of the Science," Journal American Academy of Dermatology, 2011, S66-S85, 64.

Hoffmann, "Volumizing effects of a smooth, highly cohesive, viscous 20-mg/mL hyaluronic acid volumizing filler: prospective European study," BMC Dermatology, 2009, 1-9, 9.

Jesitus, "Hyaluronic acid products dominate filler market in Europe," Dermatology Times, Oct. 1, 2013, http://dermatologytimes.modernmedicine.com/dermatology-times/news/hyaluro- nic-acid-products-dominate-filler-market-Europe Accessed Oct. 1, 2014.

Jones et al., "Volumizing Hyaluronic Acid Filler for Midface Volume Deficit: 2-Year Results from a Pivotal Single-Blind Randomized Controlled Study," Dermatological Surgery, 2013, 1602-1612, 39, Wiley Periodicals, Inc.

Jones, "Volumizing the Face With Soft Tissue Fillers," Clinical Plastic Surgery, 2011, 379-390, 38.

Juvederm Voluma XC Approval Letter, Food and Drug Administration, Oct. 22, 2013, 5 pages.

Meeting of the General and Plastic Surgery Devices Panel FDA Advisory Committee Briefing Document, Mar. 2, 2013.

Pontius et al., "Midface Injectable Fillers—Have They Replaced Midface Surgery?," Facial Plastic Surgery Clinic North America, 2013, 229-239, 21, Elsevier Inc.

Raspaldo et al., "How to achieve synergy between volume replacement and filling products for global facial rejuvenation," Journal of Cosmetic and Laser Therapy, 2011, 77-86, 13:2.

Raspaldo et al., "Longevity of effects of hyaluronic acid plus lidocaine facial filler," Journal of Cosmetic Dermatology, 2010, 11-15, 9(1), Wiley Periodicals, Inc.

Recently-Approved Devices, Juvederm Voluma XC—P110033, Food and Drug Administration, Oct. 22, 2013, http://www.fda.gov/MedicalDevices/ProductsandMedicalProcedures/DeviceApprovalsandClearances/Recently-ApprovedDevices/ucm374231.htm.

Shaw et al., "Aging of the Facial Skeleton: Aesthetic Implications and Rejuvenation Strategies," Plastic and Reconstructive Surgery, 2011, 374-383, vol. 127, No. 1, American Society of Plastic Surgeons.

Weinkle et al., "A multi-center, double-blind, randomized controlled study of the safety and effectiveness of Juvederm injectable gel with and without lidocaine," Journal of Cosmetic Dermatology, 2009, 205-210, 8(3), Wiley Periodicals, Inc.

Weinkle et al., "Attitudes, Awareness, and Usage of Medical Antiaging Treatments," The Journal of Clinical Aesthetic Dermatology, Sep. 2010, 30-33, vol. 3 No. 9.

Anonymous. "Juvederm brochure 8 point lift", Jul. 7, 2014 (Jul. 7, 2014), pp. 2, 10-11, XP055245588, Retrieved from the Internet: URL:http://www.slideshare.net/dokterfrodo/juvederm-brochure-8points?next slideshow=1 [retrieved on Jan. 28, 2016].

* cited by examiner

METHOD FOR IMPROVING DURATION OF EFFECT OF DERMAL FILLER TREATMENT

CROSS-REFERENCE TO RELATED APPLICATIONS

This application is a divisional patent application of U.S. Application Ser. No. 14/929,053, filed on Oct. 30, 2015, issued as U.S. Pat. No. 10,493,014, which claims the benefit of priority to U.S. Application No. 62/073,786 filed on Oct. 31, 2014, and U.S. Application No. 62/115,705, filed on Feb. 13, 2015, the entire contents of each of these applications being incorporated herein by this specific reference.

BACKGROUND

Field

The present invention generally relates to methods of aesthetic treatment of the face using injectable dermal fillers, and more specifically relates to methods for improving duration of effect of dermal filler treatment, for example, for treatment of midface volume deficit (MVD).

Description of the Related Art

JUVÉDERM® VOLUMA XC is a hyaluronic acid-based dermal filler implant approved in the United States for correction of age-related volume loss in the midface region in adults.

Age-related volume loss of skin, bone, and both deep and superficial fat contribute to visible signs of midface aging. In recent years, there has been a trend of patients opting for treatment with injectable fillers, when appropriate, rather than surgery for the treatment of midface volume deficit. Injectable fillers may be preferred by consumers because they are less invasive than surgery, minimizing both costs and recovery time; further, younger patients tend to choose fillers in an effort to delay surgery. In a survey conducted by the American Society for Dermatologic Surgery, consumers expressed the highest level of satisfaction with dermal fillers (92% of the time), and more than half of respondents (53%) said that they were considering future treatment with soft-tissue fillers.

Key desirable features for facial fillers include the provision of predictable and natural results that are long-lasting without being permanent. A variety of injectable fillers have been used to correct age-related midface volume deficits, although, until recently, use of fillers for this indication in the United States has been off-label. Hyaluronic acid (HA) gels are the most commonly used injectable fillers in the United States and the European Union and have an established record of safety and effectiveness. Should complications occur, one advantage of HA gels is that their effects can be reversed with hyaluronidase. The addition of lidocaine to some HA formulations reduces procedural pain and enhances patient comfort without affecting the product's safety, effectiveness, or longevity.

JUVÉDERM® VOLUMA XC (Allergan, Inc., Irvine, CA), is a crosslinked HA-based dermal filler gel containing lidocaine. This product was approved by the United States Food and Drug Administration (FDA) specifically for the correction of age-related volume loss in the midface region in adults older than 21 years of age. JUVÉDERM® VOLUMA XC is the first injectable filler to be granted FDA approval for this indication. It is a sterile, biodegradable, viscoelastic gel implant having a HA concentration of 20-mg/mL of HA, and made of a mixture of a low molecular weight HA and a high molecular weight HA, which allows for efficient crosslinking, in combination with 0.3% lidocaine. JUVÉDERM® VOLUMA XC is particularly, but not exclusively, suitable for volumizing the midface region.

SUMMARY

The present invention provides advantageous methods for using a crosslinked, hyaluronic acid based dermal filler, such as JUVÉDERM® VOLUMA XC, in the treatment of age- or disease-related midface volume deficit (MVD). It has been discovered that substantial, meaningful improvement in duration of effect of dermal filler treatment for MVD can be achieved using the present methods.

In some aspects, the present invention provides methods of treatment, for example, injection techniques, that prolong the effectiveness of a dermal filler when used to treat MVD, and reduce the amount of filler required to achieve desired correction results.

In one embodiment, a method of improving duration of effect of a dermal filler treatment of a face is provided.

As the terms are used herein, the face includes a zygomaticomalar region which includes both a left zygomaticomalar region and a right zygomaticomalar region, an anteromedial cheek which includes both a left anteromedial cheek and a right anteromedial cheek, and a submalar region which includes both a left submalar region and a right submalar region.

In one aspect, the method comprises the steps of administering a dermal filler into the face in a sequence.

In one embodiment, the sequence comprises firstly, injecting a first volume of a dermal filler into the zygomaticomalar region of the face prior to injecting further dermal filler into either or both of the anteromedial cheek and submalar region. For example, in some embodiments, the method comprises subsequently, or secondly, injecting a second volume of the dermal filler into the anteromedial cheek and thirdly, injecting a third volume of the dermal filler into the submalar region. The method maintains improvement in facial volume for an extended period of time relative to an otherwise identical method that includes injecting a total of the first, second and third volumes of an identical dermal filler into one or more of the regions, without injecting in the sequence.

Preferably, the injection into the zygomaticomalar region, that is, the injection of the first volume, comprises a supraperiosteal injection. In some embodiments, the injection of the first volume comprises a supraperiosteal injection into the right zygomaticomalar region and a supraperiosteal injection into the left zygomaticomalar region.

In some embodiments, the injection into the anteromedial cheek, that is, the injection of the second volume, comprises a supraperiosteal injection. In some embodiments, the injection of the second volume comprises a supraperiosteal injection into the right anteromedial cheek and a supraperiosteal injection into the left anteromedial cheek.

In some embodiments, the injection into the submalar region, that is, the injection of the third volume, comprises a subdermal or subcutaneous injection. In some embodiments, the injection of the third volume comprises a subdermal or subcutaneous injection into the right submalar region and a subdermal or subcutaneous injection into the left submalar region.

In some embodiments, the first volume injected is greater than about 1.4 mL. For example, the first volume is greater than about 1.4 mL and up to about 2.0 mL. For example, the first volume may be about 1.9 mL.

In some embodiments, the second volume is greater than about 1.3 mL. For example, the second volume is greater than about 1.3 mL and up to about 1.9 mL. In some embodiments, the second volume is about 1.7 mL.

In some embodiments, the third volume is greater than about 1.4 mL. For example, the third volume may be greater than about 1.4 mL and up to about 2.1 mL. For example, the third volume may be about 2.0 mL.

In some embodiments, the first volume is greater than about 1.4 mL and up to about 2.0 mL, the second volume is greater than about 1.3 mL and up to about 1.9 mL, and the third volume is greater than about 1.4 mL and up to about 2.1 mL.

In another aspect of the invention, a method of treating midface volume deficit of a patient in need thereof is provided. The method may comprise administering a dermal filler into the face comprising initially injecting a first volume of a dermal filler into a zygomaticomalar region of the face and after the injecting of the first volume into the zygomaticomalar region, injecting a second volume of the dermal filler into at least one of the anteromedial region and the submalar region. In some embodiments, the method maintains improvement in facial volume, or reduces the appearance of the midface for an extended period of time relative to an otherwise identical method that includes injecting an identical dermal filler into at least one of the anteromedial region and the submalar region without the step of initially injecting a first volume into the zygomaticomalar region. The injection into the zygomaticomalar region may comprise a supraperiosteal injection, including for example, injections into both the left side and the right side of the face. In some embodiments, the second volume is introduced into the anteromedial region, for example, the left and the right anteromedial region. In this case, the method may further comprise injecting a third volume into a submalar region of the face. The step of injecting the third volume may be performed after the step of injecting the second volume.

The present methods may maintain significant, noticeable improvement in facial volume for at least about 18 months, or at least about 20 months, or at least about 22 months, or at least about 24 months.

BRIEF DESCRIPTION OF THE DRAWINGS

FIG. 3 is a graph showing Month-6 Midface Volume Deficit Scale (MVDS) responder rates stratified by injection volume quartile (Q), wherein:

*Q1, ≤1.4 mL for zygomaticomalar region, ≤1.3 mL for anteromedial cheek, and ≤1.4 mL for submalar region.

†Q2, >1.4-2.0 mL for zygomaticomalar region, >1.3-1.9 mL for anteromedial cheek, and >1.4-2.1 mL for submalar region.

555 Q3, >2.0-3.3 mL for zygomaticomalar region, >1.9-2.7 mL for anteromedial cheek, and >2.1-3.3 mL for submalar region.

§ Q4, >3.3 for the zygomaticomalar region, >2.7 for anteromedial cheek, and >3.3 for submalar region.

DETAILED DESCRIPTION

The present invention provides methods for extending or improving duration of effect of a dermal filler treatment, particularly for midface volume deficit. The present invention also provides an improved method for treating midface volume deficit in a patient in need thereof. Advantageously, in some embodiments, the method provides a way to obtain a desired level of correction of midface volume deficit using less filler than required by conventional techniques using an identical type of filler.

In accordance with one aspect of the invention, a dermal filler gel is introduced into the face, for example, supraperiostially, dermally or subdermally, at certain locations and in certain volumes to achieve treatment results that are substantially improved over conventional methods of treatment which do not have the same improved duration of effect, or that require more filler to achieve the desired correction. The present invention provides methods of treatment that will improve patient satisfaction, reduce time period between repeat treatments, and provide physicians with effective and efficient use of dermal filler gels, with less product waste.

Figure 1:
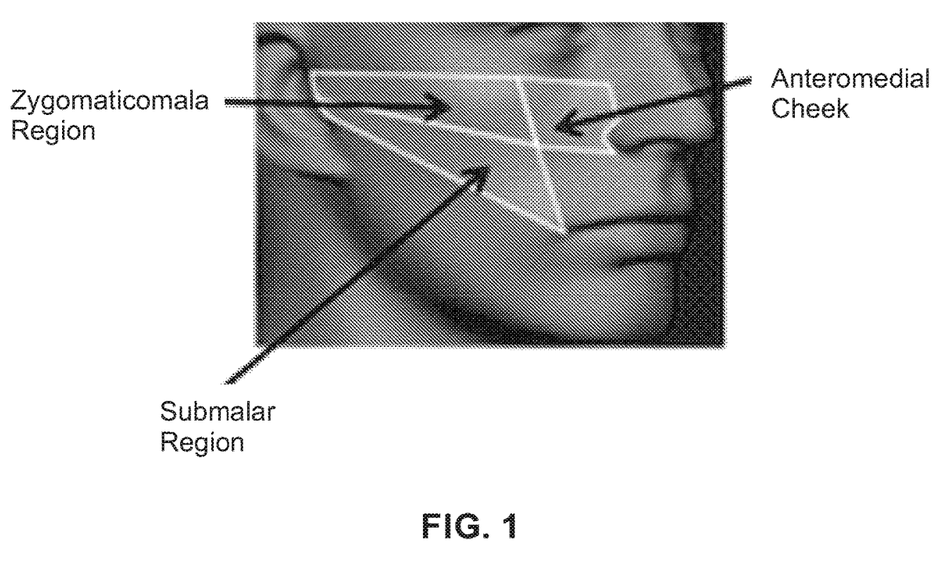
FIG. 1 illustrates three facial regions (i.e. zygomaticomalar region, anteromedial cheek, and submalar region) relevant to dermal filler treatment for midface volume deficit (MVD).

In one aspect, a method of improving duration of effect of a dermal filler treatment is provided, the method comprising injecting a dermal filler into at least one of a zygomaticomalar region, an anteromedial cheek region (hereinafter, sometimes, "anteromedial cheek"), and a submalar region, of a face, in an amount sufficient to maintain improvement in facial volume for at least 18 months, wherein the dermal filler is a crosslinked hyaluronic acid based gel. The gel may be any commercially available dermal filler gel, for example, a dermal filler available from Allergan, Inc, such as JUVÉDERM® XC injectable gel, or JUVÉDERM® VOLUMA for deep injection in the cheek area to correct age-related volume loss. FIG. 1 illustrates these three facial regions, which will be discussed in greater detail hereinafter.

In some embodiments, the injection into the zygomaticomalar region comprises an injection into the left zygomaticomalar region and an injection into the right zygomaticomalar region. In some embodiments, the injection into the anteromedial cheek comprises both a left anteromedial cheek and a right anteromedial cheek. In some embodiments, the injection into the submalar region comprises both a left submalar region and a right submalar region. The total volumes injected into the regions is the volume in total between the left and right regions or cheeks.

In one embodiment, the step of injecting comprises injecting the dermal filler into the zygomaticomalar region, and the amount injected into the zygomaticomalar region is greater than about 1.4 mL. For example, the amount injected into the zygomaticomalar region is at least about 1.4 mL to about 2.0 mL, for example, is about 1.4 mL, about 1.5 mL, about 1.6 mL, about 1.7 mL, about 1.8 mL, about 1.9 mL, or about 2.0 mL. In other embodiments, the amount injected into the zygomaticomalar region is greater than 2.0 mL, for example, is between about 2.0 mL to about 3.3 mL. In yet other embodiments, the step of injecting comprises injecting greater than about 3.3 mL in the zygomaticomalar region.

In another embodiment, the step of injecting comprises injecting the dermal filler into the anteromedial cheek, and the amount injected into the anteromedial cheek is greater than about 1.3 mL. For example, the amount injected into the anteromedial cheek is greater than about 1.3 to about 1.9. For example, the total amount injected into the anteromedial cheek may be about 1.3 mL, about 1.4 mL, about 1.5 mL, about 1.6 mL, about 1.7 mL, about 1.8 mL, or about 1.9 mL. In other embodiments, the amount injected into the anteromedial cheek is greater than about 1.9 mL and up to about 2.7 mL. In other embodiments, the amount injected is greater than about 2.7 mL.

In another embodiment, the step of injecting comprises injecting the dermal filler into the submalar region, and the amount injected into the submalar region is greater than about 1.4 mL. For example, the amount injected into the submalar region is about 2.0 mL, or at least about 2.0 mL, for example, about 2.1 mL. In one embodiment, the amount injected into the submalar region is between about 1.4 mL up to about 2.1 mL. In one embodiment, the amount injected into the submalar region is greater than about 1.4 mL and up to about 2.1 mL. For example, the amount injected into this region may be about 1.4 mL, about 1.5 mL, about 1.6 mL, about 1.7 mL, about 1.8 mL, about 1.9 mL, about 2.0 mL, or about 2.1 mL. In another embodiment, the amount injected into the submalar region is between about 2.1 mL to about 3.3 mL. In some embodiments, the amount injected into the submalar region is greater than about 3.3 mL. In some embodiment, the amount injected into this region is about 4.0 mL.

In yet another embodiment, the step of injecting comprises injecting between about 1.4 mL to about 2.0 mL of the dermal filler into the zygomaticomalar region, between about 1.3 mL to about 1.9 mL of the dermal filler into the anteromedial cheek, and between about 1.4 mL to about 2.1 mL of the dermal filler into the submalar region.

In still a further embodiment, the step of the injecting comprises injecting between about 2.0 mL to about 3.3 mL of the dermal filler into the zygomaticomalar region, between about 1.3 mL to about 1.9 mL of the dermal filler into the anteromedial cheek, and between about 2.1 mL to about 3.3 mL of the dermal filler into the submalar region.

In yet another embodiment, the step of the injecting comprises injecting between about 2.0 mL to about 3.3 mL of the dermal filler into the zygomaticomalar region, greater than 2.7 mL into the anteromedial cheek, and between about 2.1 mL to about 3.3 mL of the dermal filler into the submalar region.

In some embodiments, the first volume is greater than about 1.4 mL and up to about 2.0 mL, the second volume is greater than about 1.3 mL and up to about 1.9 mL, and the third volume is greater than about 1.4 mL and up to about 2.1 mL.

In yet a further embodiment, the step of injecting comprises injecting the dermal filler into the zygomaticomalar region, into the anteromedial cheek, and into the submalar region, in that order.

In some embodiments, the step of injecting comprises injecting greater than about 2.0 mL up to about 3.3 mL in the zygomaticomalar region, greater than about 1.3 mL up to about 1.9 mL in the anteromedial cheek, and greater than 2.1 up to about 3.3 mL in submalar region. In yet other embodiments, the step of injecting comprises injecting greater than about 3.3 mL in the zygomaticomalar region, greater than about 2.7 mL in the anteromedial cheek, and greater than about 3.3 mL in the submalar region.

In another aspect of the invention, the method maintains improvement in facial volume over baseline for at least 18 months, for at least 20 months, for at least 22 months, or for at least 24 months. In some embodiments, the method maintains improvement in facial volume for over 24 months, for example, about 25 months or 26 months.

The term "about" in the context of numerical values will be readily understood by a person skilled in the art, and preferably means that specific values may be modified by +/−10%. As regards endpoints of ranges, the modifier "about" preferably means that the lower endpoint may be reduced by 10% and the upper endpoint increased by 10%. It is also contemplated that each numerical value or range disclosed in this application can be absolute, i.e. that the modifier "about" can be deleted.

EXAMPLE

A multicenter, single-blind, randomized, controlled study was conducted in 282 subjects with MVD: 235 subjects in the treatment arm and 47 subjects in the no-treatment control arm.

More particularly, subjects aged 35 to 65 years who desired cheek augmentation to correct moderate, significant, or severe age-related MVD were treated with a crosslinked HA based dermal filler, specifically, JUVÉDERM® VOLUMA XC dermal filler. Subjects in the treatment group were predominantly female (80.4%) and represented a range of ethnic groups, with all Fitzpatrick skin types represented (see Table 1).

TABLE 1

| Demographic and Treatment Characteristics (N = 235) | |
|---|---|
| Characteristic | Value |
| Sex, n (%) Female Male | 189 (80.4) |
|  | 46 (19.6) |
| Age, median (range) | 56.0 (35-65) |
| Race, n (%) | |
| White | 137 (58.3) |
| Black | 44 (18.7) |
| Hispanic | 35 (14.9) |
| Asian | 9 (3.8) |
| Other | 10 (4.3) |
| Fitzpatrick skin type, n (%) | |
| I | 6 (2.6) |
| II | 62 (26.4) |
| III | 67 (28.5) |

TABLE 1-continued

Demographic and Treatment Characteristics (N = 235)

| Characteristic | Value |
|---|---|
| IV | 43 (18.3) |
| V | 44 (18.7) |
| VI | 13 (5.5) |
| Injection plane, n* (%) | |
| Zygomaticomalar (n = 226) | |
| Subcutaneous and supraperiosteal | 152 (67.3) |
| Only subcutaneous | 27 (11.9) |
| Only supraperiosteal | 47 (20.8) |
| Anteromedial cheek (n = 224) | |
| Subcutaneous and supraperiosteal | 123 (54.9) |
| Only subcutaneous | 21 (9.4) |
| Only supraperiosteal | 80 (35.7) |
| Submalar (n = 216) | |
| Subcutaneous and supraperiosteal | 53 (24.5) |
| Only subcutaneous | 158 (73.1) |
| Only supraperiosteal | 5 (2.3) |

*Injection plane data missing for 1 subject who was injected

The filler was introduced by injection in at least 1 of 3 facial subregions, that is, in at least one of the zygomaticomalar region, anteromedial cheek region, and submalar region, with touch-up treatment available 30 days later.

These facial regions are shown generally in FIG. 1. To identify these regions, Hinderer's lines can be marked on the patient's face to define the zygomaticomalar, anteromedial cheek, and submalar regions. More specifically, for example, a vertical line is drawn from the lateral canthus to the oral commissure, and an intersecting line is marked from the tragus to the upper alar lobule.

Figure 2:
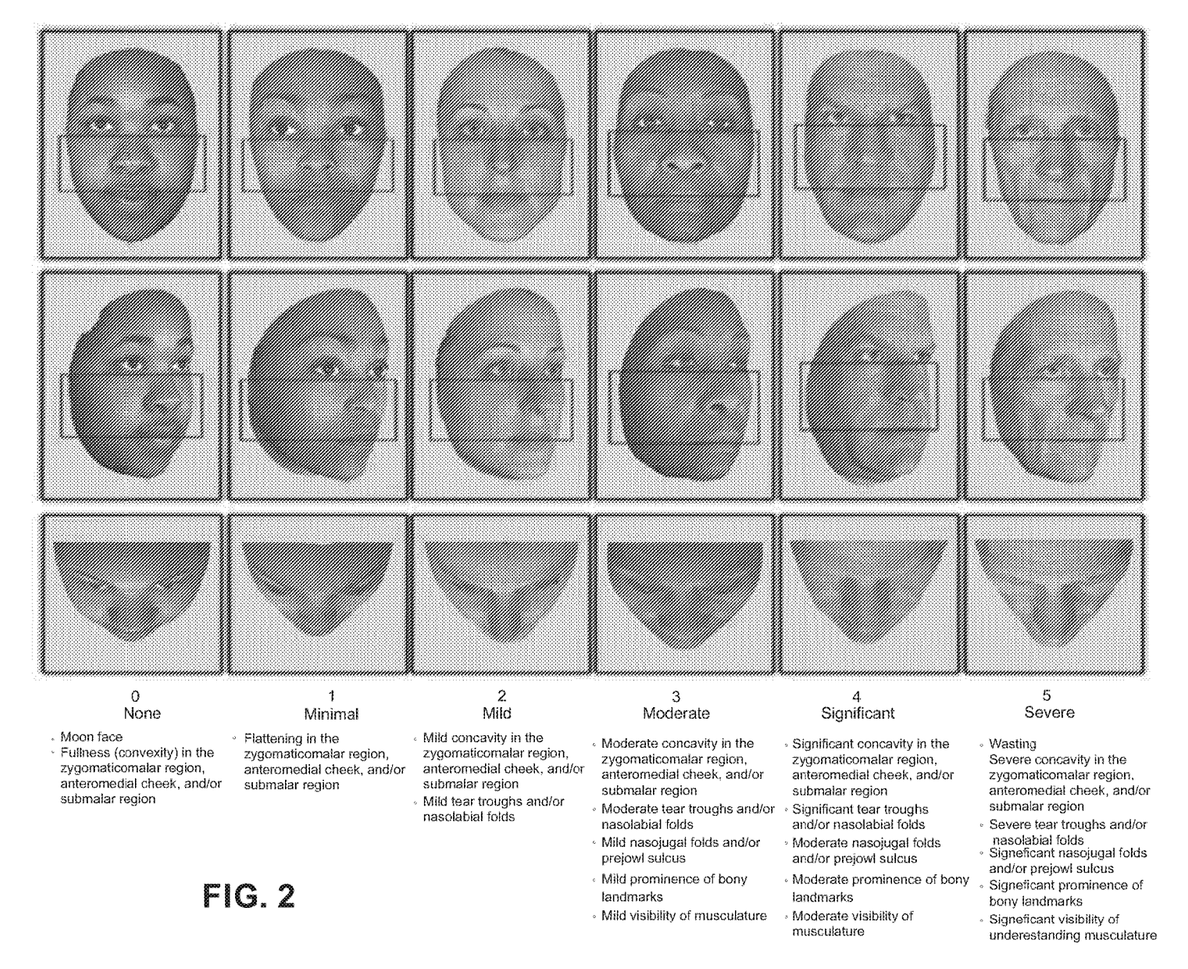
FIG. 2 is a Midface Volume Deficit Scale (MVDS) used in a study relevant to the present invention.

The primary endpoint was based on the blinded independent evaluating investigators' live assessments of subjects' overall MVD on the validated 6-point Midface Volume Deficit Scale (MVDS) (FIG. 2). Scale grades were severe (5), significant (4), moderate (3), mild (2), minimal (1), and none (0).

To be considered a "responder," the average of the two evaluating investigators' month 6 assessments had to be improved (reduced) by 1 point or more from the average pretreatment assessments. The treatment was considered to be clinically effective if 70% or more of the treatment group subjects were responders at month 6 based on a two-sided exact binomial test at 2.5% significance level and if their responder rate was statistically superior to the control group responder rate using a two-sided, two-group Fisher exact test at 2.5% significance level.

Secondary endpoints were the MVDS responder rate in each facial subregion and the responder rate on the 5-point Global Aesthetic Improvement Scale (GAIS), both based on the average of the evaluating investigators' assessments at month 6. For GAIS ratings, evaluating investigators and subjects compared the live post-treatment face with a baseline photograph and assigned the level of improvement in cheek volume as much improved (2), improved (1), no change (0), worse (−1), or much worse (−2).

In this study, 85.6% of subjects treated were Midface Volume Deficit Scale (MVDS) responders (defined as a ≥1-point improvement in MVDS scores) at 6 months. Most (85.2%) subjects were responders at 12 months, and more than two-thirds (67.1%) remained responders at 2 years.

Six-month responder rates were 75.5%, 83.2%, and 76.9% for the zygomaticomalar region, anteromedial cheek, and submalar region, respectively.

Higher responder rates were observed with increasing injection volume quartiles for each subregion. Similar median injection volumes (about 2.0 mL total) of JUVÉDERM® VOLUMA XC provided correction durations of 15-24 months: 24 months for anteromedial cheek, 19 months for zygomaticomalar, and 15 months for submalar subregions. Subject satisfaction was high across injection volume quartiles. No unanticipated treatment site adverse reactions occurred.

For each facial subregion, 2 blinded investigators assessed MVD based on the MVDS with severity scores ranging from 0 (none) to 5 (severe). Response in each facial subregion was defined as ≥1-point reduction (improvement) in MVDS score derived from the average of the 2 evaluating investigators' Month 6 assessment scores compared with their average baseline pretreatment assessments in that subregion. For each facial subregion, 6-month responder rates (i.e., percent of subjects who were responders) were stratified by injection volume quartile, with values representing the sum of initial plus touch-up injection volumes in that subregion for both sides of the face.

The degree of correction (i.e., MVDS improvement from baseline) in each subregion at 1 month for each injection volume quartile in that region was also determined to quantify the initial effect of the treatment in that region. Responder rates were calculated based on the percentage of subjects who attained specified degrees of MVDS correction (≥1-, ≥1.5-, and ≥2-point improvement from baseline).

The duration of effectiveness of the treatment for each facial subregion was established according to injection volume quartile using a Kaplan-Meier estimate of the probability of maintaining a ≥1-point improvement in MVDS score since the baseline assessment.

Subject assessment of overall aesthetic improvement in the cheeks for each injection volume quartile was assessed at 6 months with the 5-point Global Aesthetic Improvement Scale (GAIS; ratings ranging from Much Improved to Much Worse).

Subject assessment of satisfaction with overall facial appearance was assessed with the Facial Appearance Evaluation (ratings ranging from 0 [Not at All Satisfied] to 4 [Completely Satisfied]), which was patterned after Alsarrafs validated instruments. Mean scores were calculated (up to 4 points) from responses to the 6 questions on the Facial Appearance Evaluation and then multiplied by 25 and averaged to yield an overall satisfaction score ranging from 0 (Least Satisfaction) to 100 (Greatest Satisfaction).

Overall, 227 subjects (96.6%) received initial treatment in the zygomaticomalar region, 225 (95.7%) in the anteromedial cheek, and 217 (92.3%) in the submalar region. More than half of subjects who received initial treatment of the zygomaticomalar and anteromedial cheeks were treated in both the subcutaneous and supraperiosteal planes for these subregions (see, again, Table 1). In contrast, almost three-quarters (73.1%) of subjects who received initial treatment of the submalar region were treated in the subcutaneous plane only for this subregion.

The most commonly used injection techniques included tunneling, serial puncture, fanning, and crosshatching. Serial puncture was more commonly used in the anteromedial cheeks and tunneling was more commonly used in the zygomaticomalar and submalar regions. Approximately equal proportions of subjects were treated using a 27G 0.5-inch ultra-thin-wall needle and a 25G 1-inch ultra-thin-wall needle.

Referring now to Table 2, median initial injection volumes were slightly higher (1.9 mL) in the submalar than in the zygomaticomalar region and anteromedial cheek (each 1.5 mL). The percentage of subjects who required touch-up treatment of the submalar region following initial therapy was lower (55.3%) than in the zygomaticomalar region (68.3%) and anteromedial cheek (65.8%). Nonetheless, initial plus touch-up treatment volumes overall were similar for each of the 3 facial subregions.

TABLE 2

Injection Volume Overall and According to Facial Subregion

| Subregion | Initial Treatment (n = 235) | Touch-up Treatment (n = 194) | Initial and Touch-up Combined (N = 235) |
|---|---|---|---|
| Overall, median (range), mL | 4.80 (1.0-12.0) | 1.70 (0.1-7.0) | 6.50 (1.2-13.9) |
| Zygomaticomalar, median (range), mL | 1.50 (0.1-7.0) | 1.00 (0.1-3.6) | 2.00 (0.1-7.0) |
| Anteromedial cheek, median (range), mL | 1.50 (0.3-4.8) | 0.60 (0.0-2.8) | 1.90 (0.4-5.7) |
| Submalar, median (range), mL | 1.90 (0.2-8.0) | 0.80 (0.1-3.0) | 2.10 (0.2-10.0) |

Month 6 MVDS responder rates were 75.5% for the zygomaticomalar region, 83.2% for the anteromedial cheek, and 76.9% for the submalar region. Stratification of data from the treated population by injection volume quartiles is shown in FIG. 3.

Figure 3:
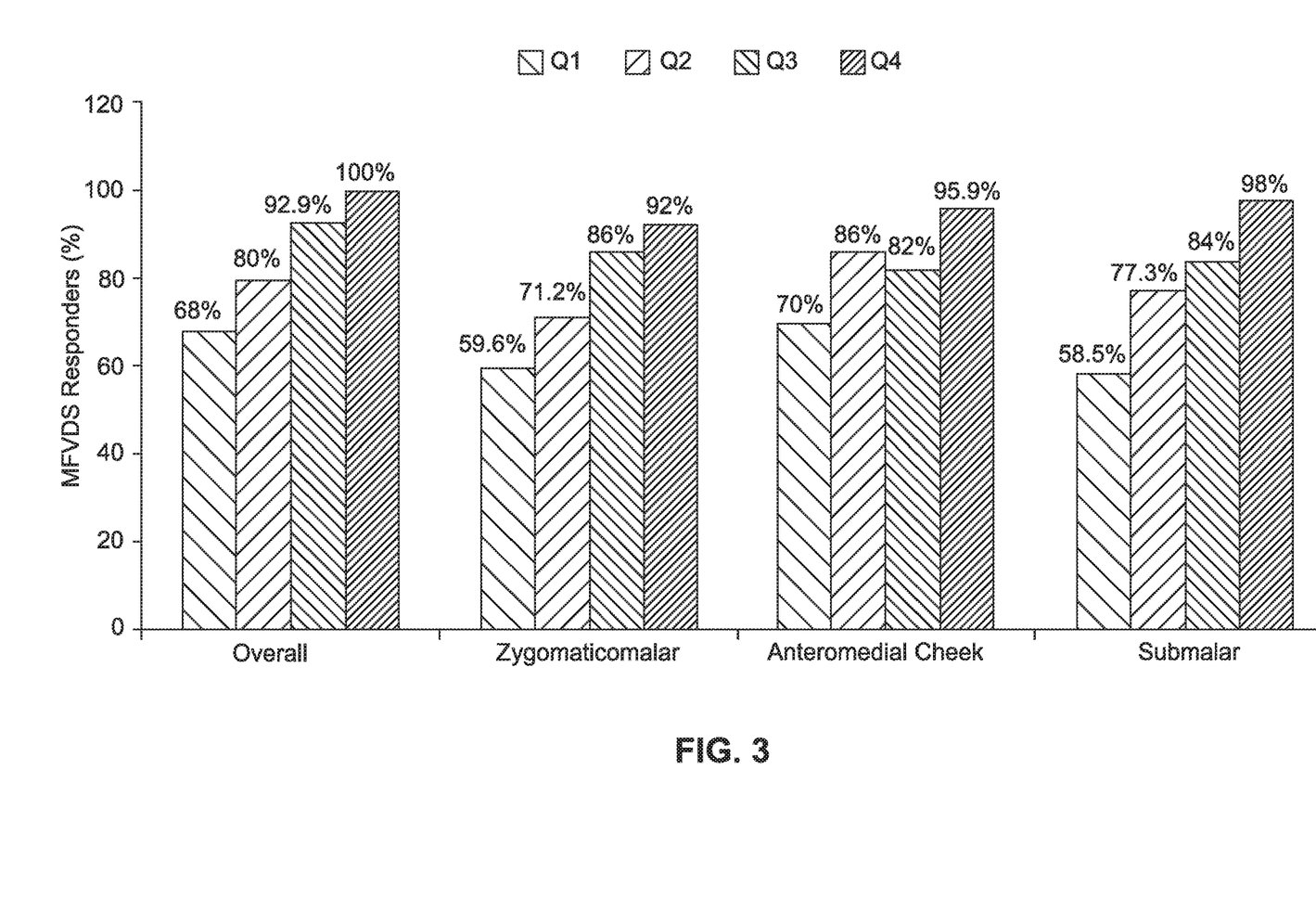

FIG. 3 is a graph showing Month-6 Midface Volume Deficit Scale (MVDS) responder rates stratified by injection volume quartile (Q). Injection volume quartiles (Q1, Q2, Q3, and Q4) are as follows:

* Q1, ≤1.4 mL for zygomaticomalar region, ≤1.3 mL for anteromedial cheek, and ≤1.4 mL for submalar region.
† Q2, >1.4-2.0 mL for zygomaticomalar region, >1.3-1.9 mL for anteromedial cheek, and >1.4-2.1 mL for submalar region.
‡ Q3, >2.0-3.3 mL for zygomaticomalar region, >1.9-2.7 mL for anteromedial cheek, and >2.1-3.3 mL for submalar region.
§ Q4, >3.3 for the zygomaticomalar region, >2.7 for anteromedial cheek, and >3.3 for submalar region.

Interestingly, higher 6-month responder rates were generally observed with increasing injection volume quartiles for each facial subregion, except for the anteromedial cheek, for which responder rates were higher with injection volumes from quartile 2 (>1.3 to 1.9 mL; 86%) than with injection volumes from quartile 3 (>1.9 to 2.7 mL; 82%).

Examining responders at higher MFVDS thresholds at Month 1 showed that higher injection volumes by quartile were associated with greater response rates at each threshold for the zygomaticomalar and submalar regions. This may be better understood with reference to Table 3, below.

TABLE 3

Month 1 Mid-Face Volume Deficit Scale Responder Rates at Increasing Thresholds Based on Evaluating Investigator Assessments and Stratified by Injection Volume Quartile (Q)

| Subregion | Injection Volume Quartile | | | |
|---|---|---|---|---|
| Zygomaticomalar (%; n/N) | | | | |
| | Q1: ≤1.4 mL | Q2: >1.4-2.0 mL | Q3: >2.0-3.3 mL | Q4: >3.3 mL |
| ≥1 point | 74.1 (40/54) | 81.3 (39/48) | 89.6 (43/48) | 92.2 (47/51) |
| ≥1.5 points | 33.3 (18/54) | 62.5 (30/48) | 70.8 (34/48) | 80.4 (41/51) |
| ≥2 points | 16.7 (9/54) | 39.6 (19/48) | 50.0 (24/48) | 54.9 (28/51) |
| Anteromedial cheek (%; n/N) | | | | |
| | Q1: ≤1.3 mL | Q2: >1.3-1.9 mL | Q3: >1.9-2.7 mL | Q4: >2.7 mL |
| ≥1 point | 72.7 (32/44) | 85.5 (47/55) | 86.0 (43/50) | 100 (48/48) |
| ≥1.5 points | 65.9 (29/44) | 74.5 (41/55) | 68.0 (34/50) | 87.5 (42/48) |
| ≥2 points | 43.2 (19/44) | 61.8 (34/55) | 52.0 (26/50) | 68.8 (33/48) |
| Submalar (%; n/N) | | | | |
| | Q1: ≤1.4 mL | Q2: >1.4-2.1 mL | Q3: >2.1-3.3 mL | Q4: >3.3 mL |
| ≥1 point | 68.5 (37/54) | 81.4 (35/43) | 90.2 (46/51) | 91.3 (42/46) |
| ≥1.5 points | 33.3 (18/54) | 69.8 (30/43) | 76.5 (39/51) | 84.8 (39/46) |
| ≥2 points | 9.3 (5/54) | 44.2 (19/43) | 54.9 (28/51) | 73.9 (34/46) |

In the anteromedial cheek, there was a general pattern of increasing responder rates at greater injection volumes, except for cut-offs of 1.5 and 2.0 improvement points, for which higher responder rates were observed with quartile 2 injection volumes (>1.3 to 1.9 mL) compared with that found with quartile 3 injection volumes (>1.9 to 2.7 mL).

Figure 4:
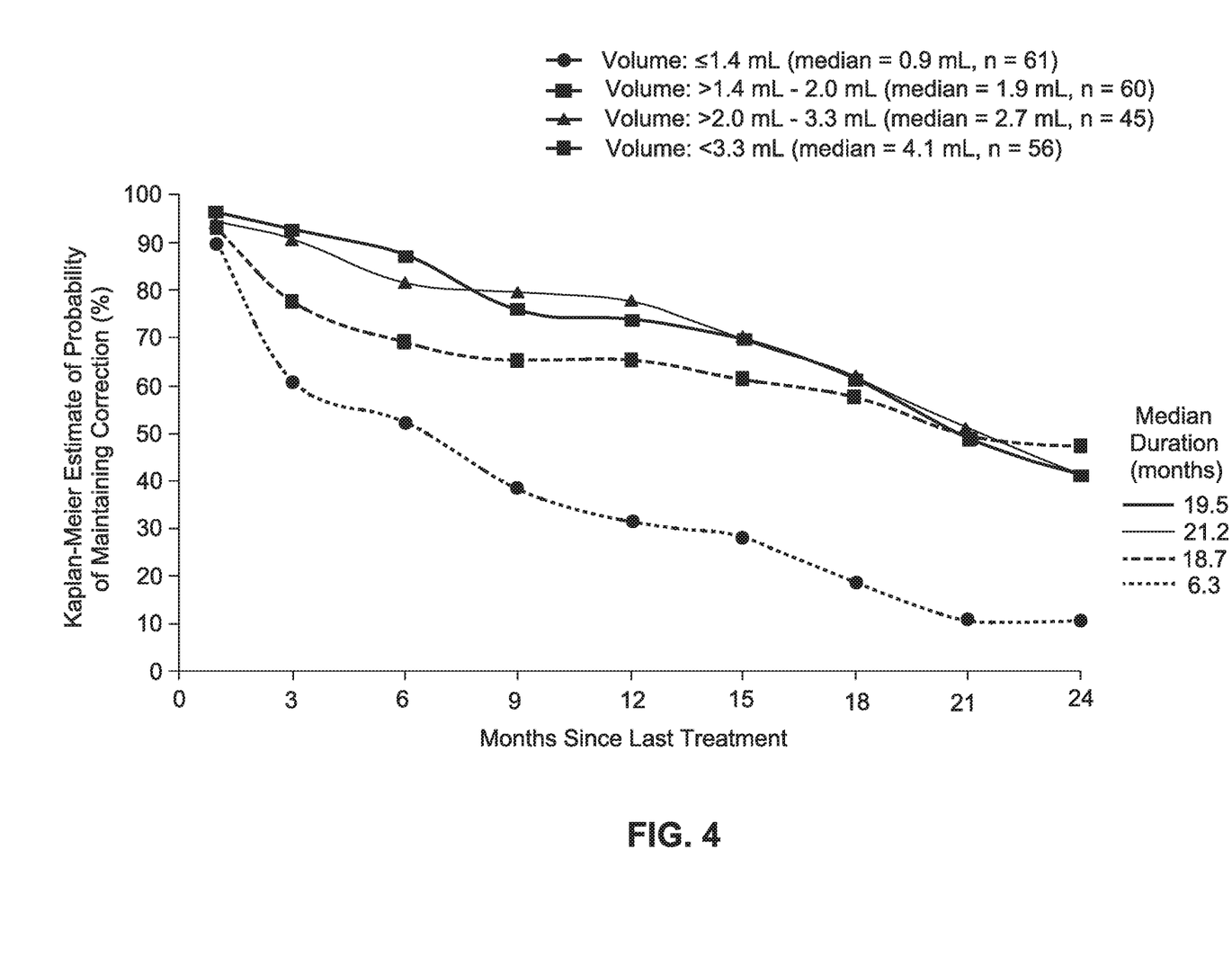
FIG. 4 is a graph showing duration of effectiveness of a crosslinked HA based dermal filler in the zygomaticomalar region by injection volume quartile.
Figure 5:
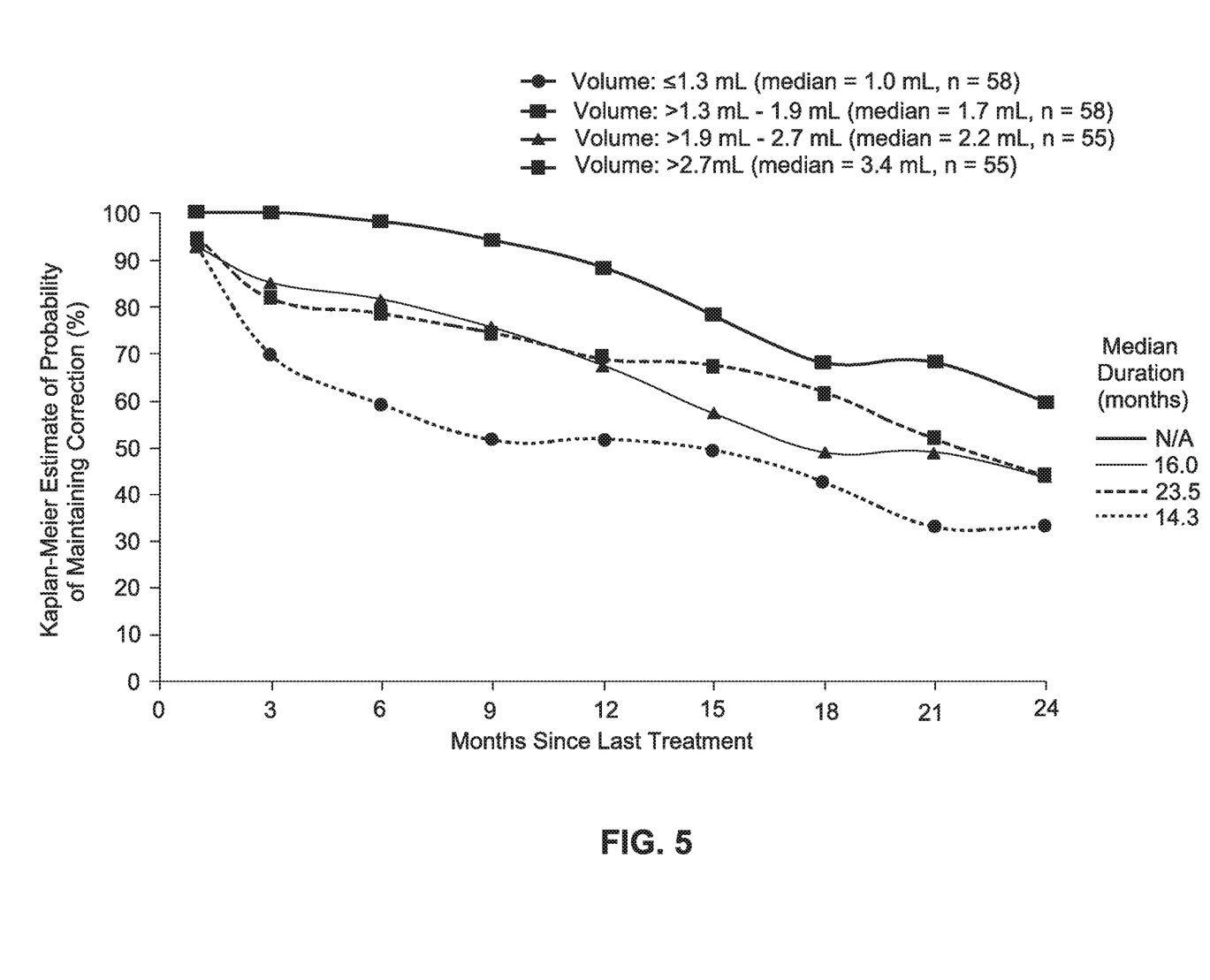
FIG. 5 is a graph showing duration of effectiveness of the dermal filler in the anteromedial cheek by injection volume quartile. The median duration could not be determined since the estimated probability of maintaining correction never reached 50%.
Figure 6:
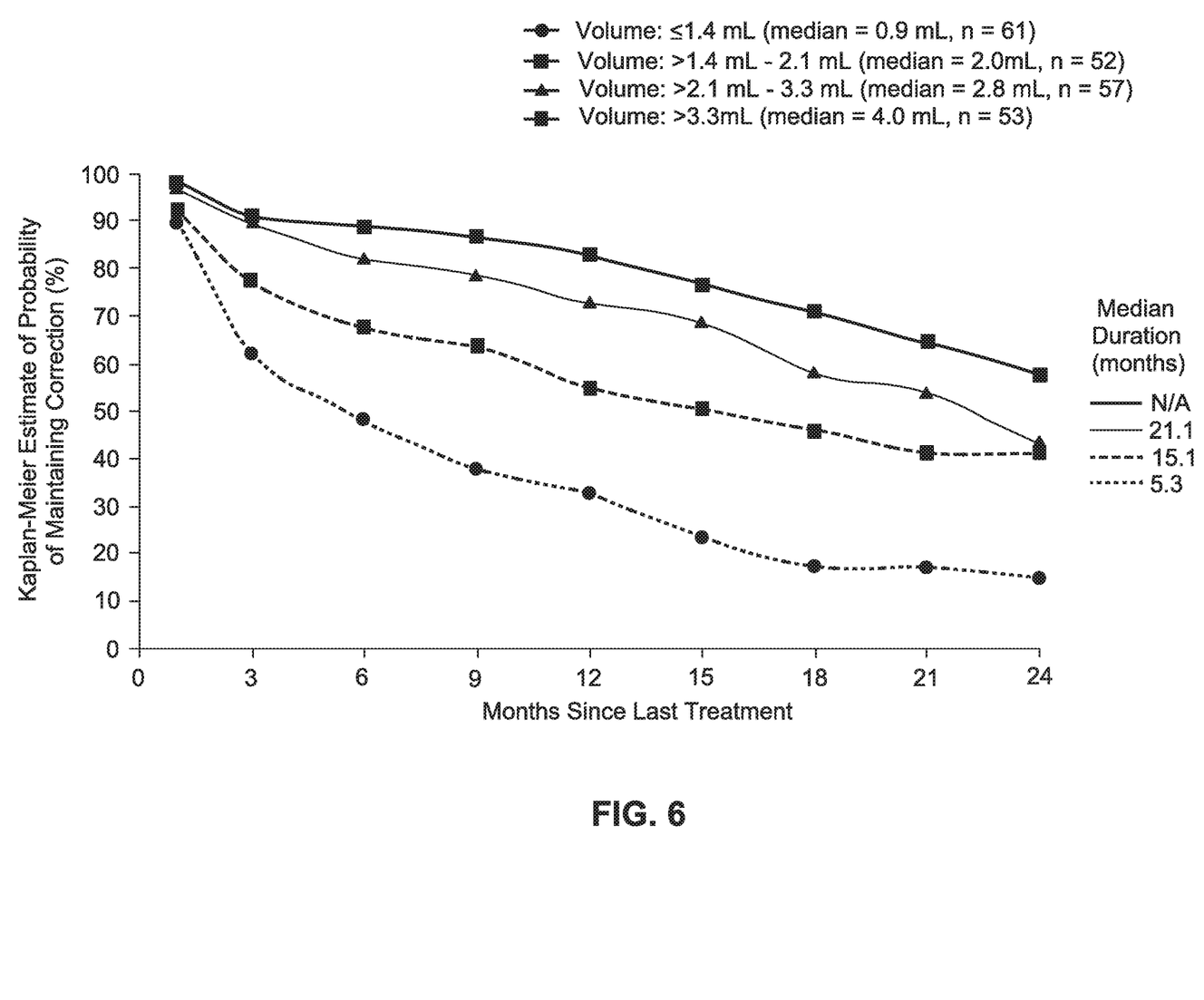
FIG. 6 is a graph showing duration of effectiveness of the dermal filler in the submalar region by injection volume quartile. The median duration could not be determined since the estimated probability of maintaining correction never reached 50%.

For each facial subregion, the duration of effect of the treatment was stratified by injection volume (FIGS. 4-5). Interestingly, the longest observed median duration of effect occurred with injection volumes of >2.0 to 3.3 mL (quartile 3) in the zygomaticomalar region (21.2 months), >1.3 to 1.9 mL (quartile 2) in the anteromedial cheek (23.5 months), and >2.1 to 3.3 mL (quartile 3) in the submalar region (21.1 months).

It is noted that median duration could not be observed in the highest quartiles in the anteromedial cheek (>2.7 mL) and submalar region (>3.3 mL) because the estimated probability of maintaining correction never reached 50% at these quartiles. This indicates that the median duration of effect of the treatment at these injection volumes was greater than 24 months.

The injection of approximately 2 mL of JUVÉDERM® VOLUMA XC in each respective facial subregion had a duration of effect lasting between 15.1 and 23.5 months: 18.7 months for zygomaticomalar, 23.5 months for anteromedial cheek, and 15.1 months for submalar. This is evident from the median injection volume and the median duration of effect observed for subjects in quartile 2 of each subregion.

Figure 7:
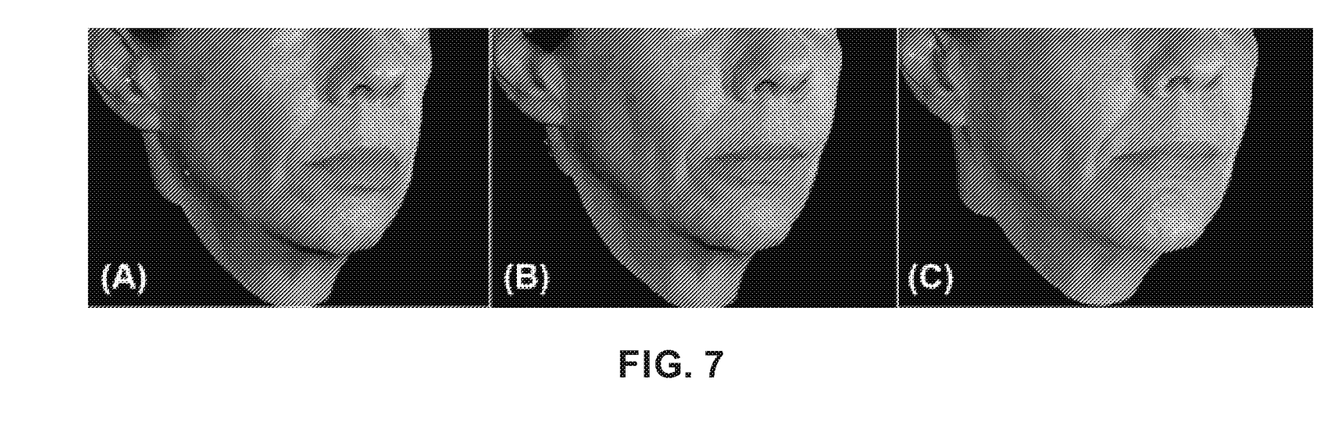
FIG. 7 are photos showing aesthetic outcomes for a woman treated for MVD.
Figure 8:
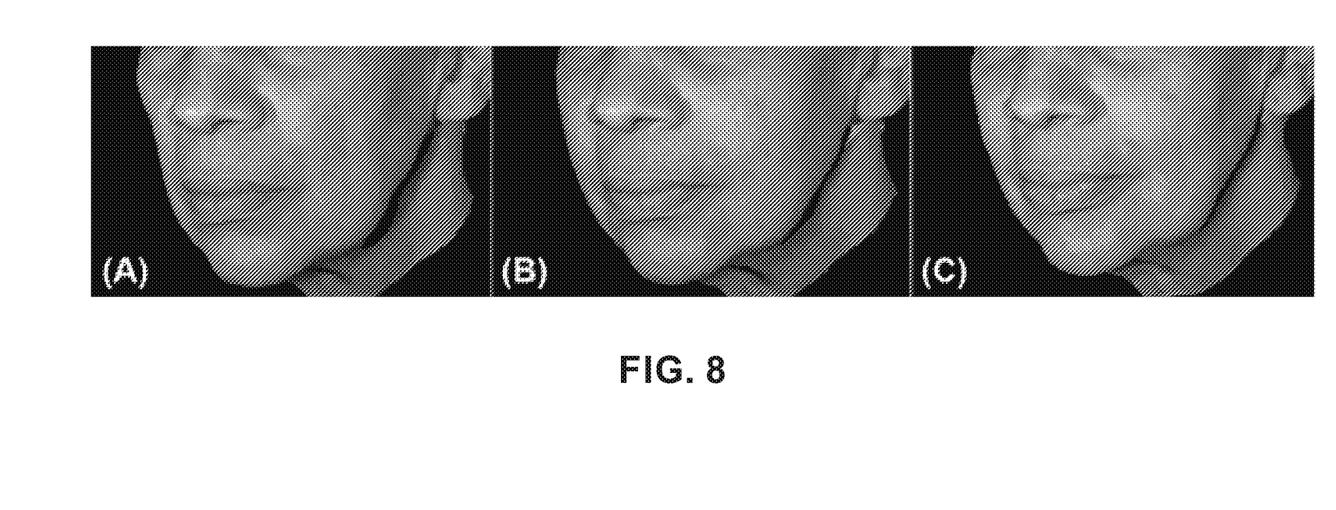
FIG. 8 are photos showing aesthetic outcomes for another woman treated for MVD.
Figure 9:
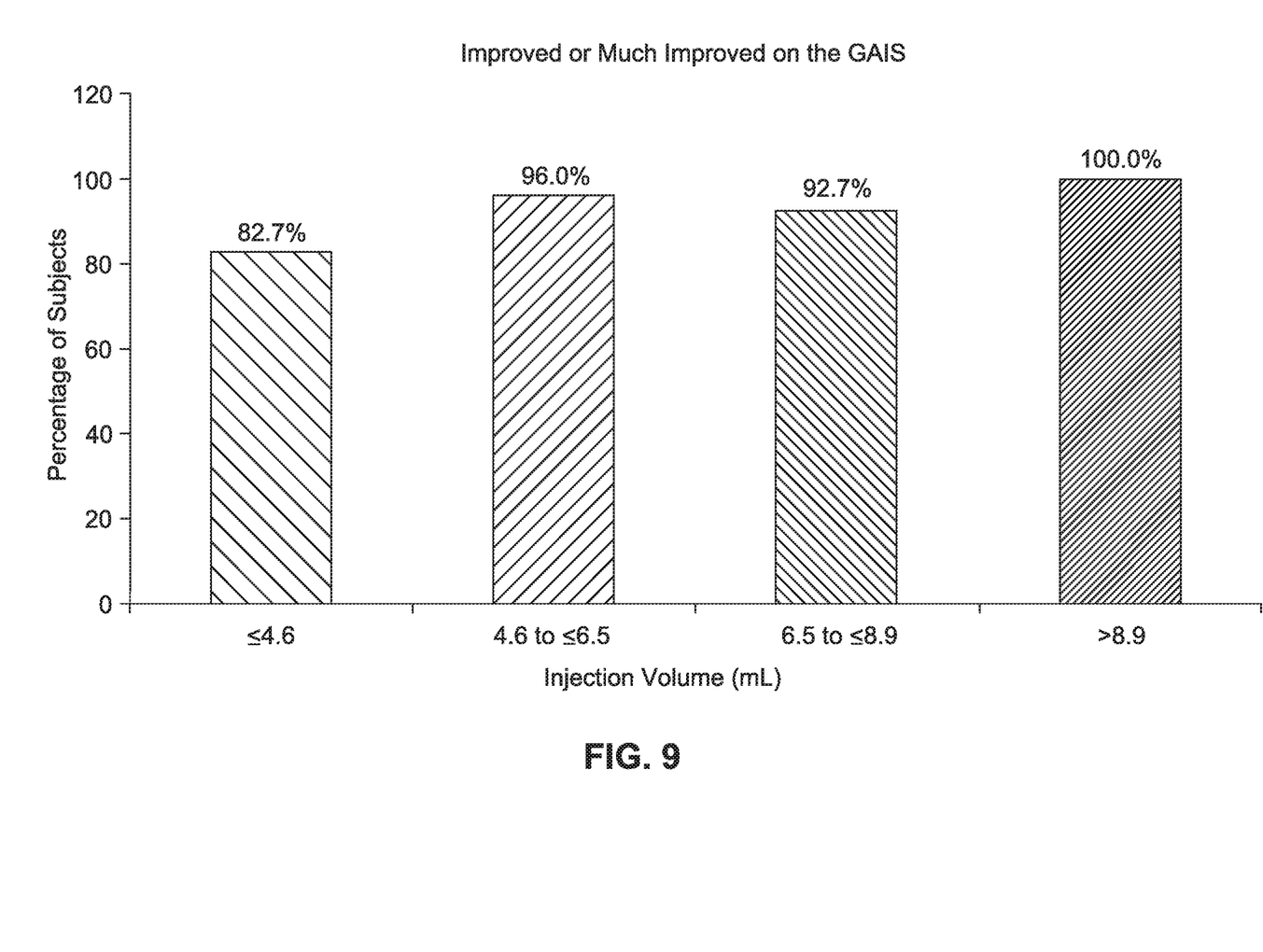
FIG. 9 is a graph showing subject ratings on the Global Aesthetic Improvement Scale (GAIS) by overall injection volume quartile: percent of subjects Improved or Very Much Improved at Month 6.
Figure 10:
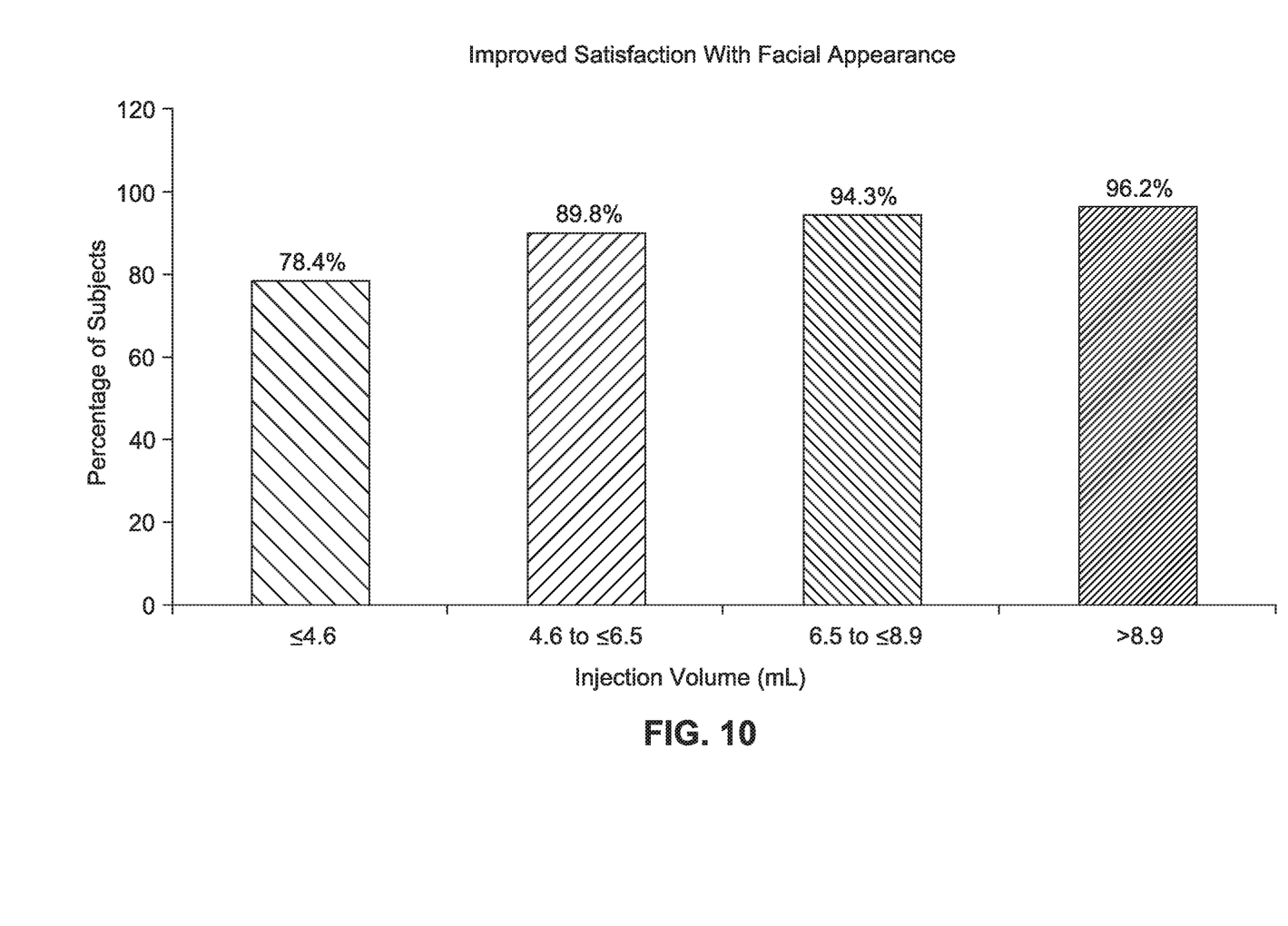
FIG. 10 is a graph showing subject ratings on the Facial Appearance Evaluation by overall injection volume quartile: percent of subjects with improved satisfaction with facial appearance at Month 6.

The time course of effect for two individual subjects treated with different volumes of the dermal filler is shown in FIGS. 7 and 8. FIG. 7 shows aesthetic outcomes for a woman treated for MVD, a 57-year-old woman before treatment (A) and 1 (B) and 24 months (C) after the treatment at 5.4 mL injection volume (initial plus touch-up, both sides of face combined). This individual's MVDS score improved from moderate/significant at baseline to minimal at Month 1 and was mild/moderate at Month 24.

FIG. 8 shows aesthetic outcomes for a 59-year-old woman before treatment (A) and 1 (B) and 24 months (C) after the treatment at 8.9 mL injection volume (initial plus touch-up, both sides of face combined). This individual's MVDS score improved from moderate at baseline to minimal at Month 1 and was minimal/mild at Month 24.

Subject assessment of global aesthetic improvement and satisfaction with facial appearance at Month 6 was assessed with the GAIS and the Facial Appearance Evaluation, respectively, and stratified by total injection volume quartile. The percentage of subjects who rated themselves as improved or very much improved on the GAIS (82.7%, 96.0%, 92.7%, and 100.0% for quartiles ≤4.6 mL, 4.6 to ≤6.5 mL, 6.5 to ≤8.9 mL, and >8.9 mL, respectively) or as having improved satisfaction with their facial appearance (78.4%, 89.8%, 94.3%, and 96.2% for quartiles ≤4.6 mL, 4.6 to ≤6.5 mL, to ≤8.9 mL, and >8.9 mL, respectively) was high across injection volume quartiles, generally increasing as injection volume increased.

It was observed that MVDS improvement at Month 6 was similar between subjects who received initial treatment only (87.5% responder rate) and subjects who received initial as well as touch-up treatment (85.2% responder rate). Interestingly, touch-up injections may not necessarily create longer-lasting effects.

There were no unanticipated treatment-site responses. Injection-site tenderness, swelling, firmness, lumps/bumps, and bruising of mild to moderate severity were most frequently reported by subjects in each subregion, and incidence rates of these injection site responses were similar across the 3 facial subregions. Further, distribution of device-related adverse events was equal across the 3 facial subregions.

The data show Month 6 MVDS responder rates were high (75.5%-83.2%) in each facial subregion. The results of this analysis are applicable to a diverse population, considering the representation of both women and men, a broad age range, and multiple ethnicities in the study population.

Notably, despite somewhat similar median injection volumes of the filler, improved durations of correction were not linear and were notably different in the 3 facial subregions. A dose-response effect was observed in the submalar region with median duration of correction increasing with higher injection volume quartiles, but a dose-response effect was not clear in the zygomaticomalar region and the anteromedial cheek region. Relatively small injection volumes targeted to specific facial subregions, and combined with appropriate injection technique, resulted in long-lasting improvement.

The order of injection into the facial subregions may be significant in some embodiments for maximizing the treatment duration and effect. In one embodiment, the order for treatment for injection into the different facial subregions is generally the zygomaticomalar region, followed by anteromedial cheek, then submalar region. For example, the method may comprise first injecting the dermal filler against bone in the zygomaticomalar region, thus establishing a base of support before injecting into the fleshier submalar region.

In one embodiment, a method of improving duration of effect of dermal filler treatment is provided wherein the method comprises administering a dermal filler into the face in a sequence. For example, the method may comprise firstly, or prior to introducing dermal filler into the submalar region, introducing a volume of the filler in the zygomaticomalar region, for example, in the supraperiosteal plane.

For example, the method comprises firstly, injecting a first volume of a dermal filler into the zygomaticomalar region of the face, secondly, injecting a second volume of the dermal filler into the anteromedial cheek, and thirdly, injecting a third volume of the dermal filler into the submalar region. The method maintains improvement in facial volume for an extended period of time relative to an otherwise identical method that includes injecting a total of the first, second and third volumes of an identical dermal filler into one or more of the regions, without injecting in the sequence.

In another exemplary embodiment, the method comprises initially injecting a first volume of a dermal filler into at a zygomaticomalar region of the face and after the injecting of the first volume, injecting a second volume of the dermal filler into the submalar region, wherein the method maintains improvement in facial volume for an extended period of time relative to an otherwise identical method that includes injecting an identical dermal filler into the submalar region without the step of initially injecting a first volume into the zygomaticomalar region.

In some of these embodiments, the first volume is injected into the supraperiostial plane in the zygomaticomalar region. In some embodiments, the volume injected into the zygomaticomalar region, for example, in total between both a left zygomaticomalar region and a right zygomaticomalar region, is at least about 2.0 ml, or at least about 3.3 mL. In some embodiments, the first volume may be between about 2.0 mL and about 4.0 mL.

While injection of about 2.0 mL of dermal filler into each region can provide effective treatment results, embodiments of the present invention which provide different ranges of volumes in specific regions, and in some embodiments, specific orders, can provide greatly improved duration of effect, for example, can provide noticeable or desirable correction from baseline for at least 15 to about 24 months or longer, in each subregion, or for at least 18 months to 24 months and longer for the face overall.

Example Method of an Embodiment of the Invention

A 53-year old woman presents midface volume deficit (MVD). The physician administers, by injection, a commercial dermal filler comprising crosslinked hyaluronic acid. The administration is performed by first injecting about 1.9 mL in the zygomaticular region (total volume distributed between the left and right zygomaticular regions). These zygomaticular injections are done using a 30 Gauge needle, and the filler is implanted deep, for example, against the bone. Next, the physician injects about 1.7 mL into the anteromedial cheek (total volume distributed between left and right anteromedial cheeks), The physician then finally injects about 2.0 mL of the filler into the submalar region (total volume distributed between left and right submalar regions). The total amount of dermal filler administered is thus about 5.6 mL. The physician notes that the patient has an improvement of at least about 1-2 points on the MVDS compared to her face prior to treatment. The patient returns to her everyday activities immediately after the treatment. The patient reports that she notices a youthful fullness of her face, and she is happy with the treatment. She returns to the physician for a follow up visit at 24 months after treatment. The patient reports that she is still satisfied with the treatment results, and she notices an improvement in fullness at this time relative to her face pre-treatment, which is verified with pre-treatment photos. The physician compares before and after photographs of the patient and notes that the patient, at this 24 month follow up visit, has maintained a correction improvement of at least about 1 point on the MVDS. Interestingly, these good results are achieved based on only the single treatment session, with no repeated injections, "top-ups," or further injection treatment between the time of the treatment session and 24 months following the treatment.

Each and every feature or step described herein, and each and every combination of two or more of such features or steps, is included within the scope of the present invention provided that the features or steps included in such a combination are not mutually inconsistent.

What is claimed is:

1. A method of improving duration of effect of a dermal filler treatment of a face, the method comprising:
   (i) injecting a first volume of a dermal filler into a zygomaticomalar region of the face;
   (ii) injecting a second volume of the dermal filler into an anteromedial cheek of the face; and
   (iii) injecting a third volume of the dermal filler into a submalar region of the face;
   thereby improving the duration of the effect of the dermal filler treatment.

2. The method of claim 1, wherein the dermal filler is a crosslinked hyaluronic acid based gel.

3. The method of claim 1, wherein the first volume is between about 1.4 mL and about 2.0 mL, the second volume is between about 1.3 mL and about 1.9 mL, and the third volume is between about 1.4 mL and about 2.1 mL.

4. The method of claim 3, wherein the first volume is about 1.9 mL, the second volume is about 1.7 mL, and the third volume is about 2.0 mL.

5. The method of claim 1, wherein the injection into the zygomaticomalar region comprises a supraperiosteal injection.

6. The method of claim 1, wherein the injection into the anteromedial region comprises a supraperiosteal injection.

7. The method of claim 1, wherein the dermal filler comprises a crosslinked hyaluronic acid.

8. The method of claim 1, wherein the dermal filler comprises 20 mg/mL of hyaluronic acid.

9. A method of improving duration of effect of a dermal filler treatment of a face, the method comprising:
   (i) injecting between about 1.4 mL and about 3.3 mL of the dermal filler into a zygomaticomalar region of the face;
   (ii) injecting between about 1.3 mL and about 2.7 mL of the dermal filler into a anteromedial cheek of the face; and
   (iii) injecting between about 1.4 mL and about 3.3 mL of the dermal filler into a submalar region of the face;
   thereby improving the duration of the effect of the dermal filler treatment.

10. The method of claim 9, wherein the dermal filler comprises a crosslinked hyaluronic acid.

11. The method of claim 9, wherein the dermal filler comprises 20 mg/mL of hyaluronic acid.

12. The method of claim 9, wherein the dermal filler is a crosslinked hyaluronic acid based gel.

13. A method of improving duration of effect of a dermal filler treatment of a face, wherein the dermal filler comprises a crosslinked hyaluronic acid, the method comprising injecting the dermal filler into a zygomaticomalar region of the face, an anteromedial cheek of the face, and a submalar region of the face, thereby improving the duration of the effect of the dermal filler treatment.

14. The method of claim 9, wherein the dermal filler comprises 20 mg/mL of hyaluronic acid.

* * * * *